United States Patent
Nordan et al.

[11] Patent Number: 6,139,559
[45] Date of Patent: Oct. 31, 2000

[54] SURGICAL BLADE

[76] Inventors: Lee T. Nordan, 9834 Genesee, Suite 209, La Jolla, Calif. 92037; Ravi Nallakrishnan, 26 Plaza Dr., Westmont, Ill. 60559

[21] Appl. No.: 09/056,382

[22] Filed: Apr. 7, 1998

[51] Int. Cl.[7] ........................................... A61F 9/00
[52] U.S. Cl. ..................... 606/166; 606/167; 606/170; 606/180
[58] Field of Search ........................ 606/166, 167, 606/168, 170, 172, 180, 181

[56] References Cited

U.S. PATENT DOCUMENTS

| | | | |
|---|---|---|---|
| 5,203,865 | 4/1993 | Siepser | 606/166 |
| 5,370,652 | 12/1994 | Kellan | 606/166 |
| 5,713,915 | 2/1998 | Van Heugten et al. | 606/166 |

Primary Examiner—Michael Buiz
Assistant Examiner—Lien Ngo
Attorney, Agent, or Firm—Jerry A. Schulman

[57] ABSTRACT

A surgical blade for use in ophthalmic surgery has distal cutting edges formed by a pair of anterior-to-posterior bevels which meet at an angle greater than 90° and preferably 140°, resulting in a blade with a surface area greater than that of similarly dimensioned prior art blades. An anterior shoulder is positioned intermediate the distal and proximal ends of the blade to direct the blade to dimple down when the blade has been inserted into the cornea a sufficient distance to bring the shoulder into contact with the corneal tissue, allowing the surgeon to make a reproducible, leak-free incision by using a straight-in hand motion. The distal cutting surface is rounded at its lateral edges to avoid snagging the incision when the blade is passed through the cornea.

24 Claims, 3 Drawing Sheets

SURGICAL BLADE

BACKGROUND OF THE INVENTION

1. Field of the Invention

The present invention relates generally to surgical knife blades and in particular to blades used in ophthalmological surgical procedures such as clear corneal incisions.

2. Description of the Prior Art

Ophthalmic surgeons work within a very small operating field upon organs whose tissues are complex and delicate. Cuts made during surgery must be precise as to length, direction and depth, requiring surgical knives of unsurpassed sharpness and maneuverability and with configurations particularly suited to operating upon selected portions of the eye.

It has become well-known to design blades for ophthalmological knives to perform specific cuts used in certain types of eye surgery. One type of ocular surgery used to correct cataracts is referred to as clear corneal cataract surgery, discussed in an article entitled "Beveled blades have simplified clear corneal technique" by William F. Maloney, M.D., appearing in the Sep. 15, 1997 issue of *Ocular Surgery News* in which clear corneal surgery is generally described as the use of a beveled diamond blade to make a three-step incision to form a path through the cornea and into the anterior chamber of the eye.

As mentioned by Dr. Maloney, examples of known beveled blades are the Rhein 3-D trapezoid blade manufactured by Rhein Medical, Inc. of Tampa Fla., the Accutome beveled diamond manufactured by Accutome of Malvern, Pa., the Storz multi-beveled diamond manufactured by Storz of St. Louis, Mo., and the pyramid diamond manufactured by KMI of Paoli, Pa. All feature a blade profile having a posterior surface formed generally as an elongated "home plate" type of pentagon with a leading, sharply V-shaped pointed tip, an anterior surface shaped generally to correspond to the posterior surface and a series of bevels extending from the anterior surface to the posterior surface. Cutting edges are formed where the two bevels intersect, or where a bevel intersects the anterior or posterior surface, most typically resulting in a pair of cutting edges diverging from a leading point or distal end of the blade along the legs of a V to intersect with a pair of lateral cutting edges formed along that portion of the blade extending from the distal end rearward toward the proximal end which is adapted to be gripped by a knife or blade holder. Certain known blade configurations feature lateral cutting edges that are substantially parallel while other configurations feature lateral cutting edges that diverge along the distal-to-proximal direction, allowing the width of the incision to be determined by the distance to which the blade is inserted through the corneal membranes, with the incision being widened as the blade is inserted.

Removing a damaged or diseased lens and replacing it with an artificial intraocular lens calls for the surgeon to make incisions in the cornea or the sclera through which fragments of the old lens are removed and through which the new lens is inserted. Techniques are now used to fold the new lens prior to insertion and to allow it to unfold once it is in place, requiring a relatively small, straight incision which heals quickly and, if properly made, limits or eliminates fluid leakage from the eye without requiring suturing or hydration.

The cornea is made up of several tissue layers through which an incision must be made to reach the anterior chamber of the eye, principally the anterior epithelium, Bowman's membrane and Descemet's membrane. A description of the problems inherent in making such incisions and the techniques presently required is found in U.S. Pat. No. 5,713,915 (Van Heugten, et al.). According to Van Heugten, et al., because the cornea is spherical in shape, such cuts tend to produce non-linear incision lines unless they are made at a 90° angle to the surface being cut. One presently known technique for making linear, water-tight incisions is described as "dimpling down" which requires a surgeon to attempt to flatten the cornea, or "dimple down" as soon as the tip of the surgical blade reaches Descemet's membrane in order to create a substantially linear, perpendicular incision through the membrane. According to Van Heugten, et al., dimpling down requires the surgeon to lift the back of the blade up to point the tip of the blade down which can cause distortion in the tunnel formed by the cut. Lifting the back of the blade also increases the angle of the cut, making it less tangential to the circumferential arc of the cornea, affecting the water-tight integrity of the unsutured incision. To compensate, the surgeon must hydrate the corners of the incision.

U.S. Pat. No. 5,713,915 (Van Heugten, et al.) teaches and describes a surgical knife blade for use in ophthalmological surgery characterized by sharply pointed tip and a non-symmetrical lateral profile, with cutting edges formed by the intersection of differently-sized anterior and posterior bevels to position the cutting edges closer to the anterior surface than the posterior surface. Van Heugten, et al. state that curved incisions result most directly from the use of blades that are typically symmetrical when the anterior surface is compared to the posterior surface. Also claimed in Van Heugten, et al. are side edges formed by anterior and posterior bevels, with the side edges meeting the cutting edges at a shoulder and with the side edges and the cutting edges being equal at the shoulder.

Other prior art blades used to incise the cornea characteristically have sharply pointed tips and fall generally into two categories: symmetrical blades with cutting edges formed by bevels and positioned substantially midway between anterior and posterior blade surfaces, and blades with edges formed by a bevel formed on one blade surface intersecting the plane of the other surface.

U.S. Pat. No. 4,688,570 (Kramer, et al.) teaches and describes an ophthalmological surgical instrument used to guide a knife in cutting radial keratomatic incisions in the cornea. The knives shown in Kramer, et al. are of the type having anterior and posterior bevels intersecting midway through the blade's thickness to form the cutting edges.

U.S. Pat. No. 5,201,747 (Mastel) teaches and describes an ophthalmological surgical instrument having a triple edge tip using opposed bevels to form a symmetrical blade.

U.S. Pat. No. 5,217,476 (Wishinsky) teaches and describes a surgical knife blade and method of performing cataract surgery utilizing a surgical knife blade which is symmetrical and beveled to form a centrally-positioned cutting edge.

U.S. Pat. No. 5,224,950 (Prywes) teaches and describes a color calibrated multifunction scalpel blade for intraocular and other surgery and associated methods of use showing symmetrical cutting edges and a color-coded blade to indicate how deeply the blade has been inserted.

U.S. Pat. No. 5,376,099 (Ellis, et al.) teaches and describes an undercut diamond surgical blade and method of using the same having a non-symmetrical pointed cutting tip, the cutting edges of which are centered between the two surfaces of the blade and are formed by bevels on the blade sides.

U.S. Pat. Nos. 5,203,865 and 5,098,438 (Siepser) teach and describe surgical knives for use in ophthalmic surgery and procedures for intraocular surgery in which a variety of surgical knives are described of the type having parallel surfaces and cutting edges formed by the intersection of bevels extending from one face to the other.

U.S. Pat. No. 5,370,652 (Kellan) teaches and describes a surgical knife blade for making sutureless incisions in the eye and methods therefor which discloses several blade configurations with cutting edges formed by the intersection of a posterior bevel with the anterior surface of the blade.

U.S. Pat. No. 5,405,355 (Peyman, et al.) teaches and describes a method of radial keratotomy employing a vibrating cutting blade in which a triangular blade with cutting edges formed by blade face bevels is disclosed.

U.S. Pat. No. 5,222,967 (Casebeer) teaches and describes a keratorefractive diamond blade and surgical method illustrating a blade with a cutting edge formed by intersecting blade bevels.

U.S. Pat. No. 5,336,235 (Myers) teaches and describes a keratome having a curved, pointed blade with a cutting edge formed by the intersection of a bevel on the upper, curved surface with the lower, curved surface.

These references generally exemplify surgical blades having "pointy" blade tips, that is, blades whose cutting edges meet at an acute angle. It is believed that this design creates problems when making the type of incision required for clear corneal surgery. In particular, the available surface area of the blade available to support the tissue during cutting is limited when compared to the surface area of a blade whose lead cutting edges meet at a larger angle. Adopting the cutting profile of the present invention thus teaches away from the present art because such a profile would seem to require significantly more force to start a cut, a factor that must be balanced against the advantage of having a larger surface area to support the tissues being incised. However, this has not been the case. Blades made in accordance with the teachings of the present invention have been successfully used in clear corneal surgery.

It is an object of the clear corneal surgical technique to make an incision that seals itself and does not require sutures to prevent leakage of fluid from the anterior chamber of the eye. It has been found that a single lateral incision which extends partially through the cornea and then changes to a direction more approximating a line perpendicular to Descemet's membrane creates a path or tunnel through the corneal tissue which effectively seals itself and does not leak. The first segment of this incision through the outer corneal tissue is identified as the inner corneal valve, while the second, stepped portion of the incision is called the anterior chamber entry.

It is believed that one of the keys to making such an incision self-sealing is to maximize the surface area of the cut, that is, the surface area of the "roof" and "floor" of the tunnel. Another factor is the ability to keep the incision linear, that is, to keep the edges of the incision straight, not allowing them to tear or sag down. Another problem is thought to result when the blade is withdrawn after it has pierced Descemet's membrane. There are times when the edges of the incision are torn, presumably when the edges snag on a portion of the blade as it is withdrawn or when the surgeon is required to abruptly change the angle of the blade to dimple down. Such tears cause leaks.

It is also desirable to have a blade configuration which allows the surgeon to make accurate, reproducibly self-sealing incisions without having to estimate the depth of cut and without relying upon the need to change hand positions during the incision or to estimate the angle to which the blade must be brought to effectively dimple down and complete the incision.

Accordingly, it is an object of the present invention to provide a blade to be used for ophthalmological surgical procedures that will create a reproducibly self-sealing incision when used to penetrate the corneal tissue, eliminating the need for sutures.

It is also an object of the present invention to provide such blades in configurations which maximize the surface area of the incision to enhance the self-sealing action.

It is a further object to provide such blades in configurations which support the incision as it is being made to limit the tendency of the incision edges to sag or tear.

Another object is to provide such blades in configurations which automatically create a dimpling down action at a reproducible depth of cut through the corneal tissue without requiring the surgeon to change hand positions to select an entry angle.

Still another object of the present invention is to provide such blades in configurations which reduce the tendency of the blade to snag on the edges of the incision when the blade is being withdrawn.

It is clear from the foregoing that there is a demonstrated need for a surgical blade for use in ophthalmological surgical procedures which is capable of reproducibly creating a leak-proof corneal incision through which other surgical procedures may be carried out without requiring the surgeon to make adjustments in hand position or to determine visually when or to what extent the angle of cut should be changed.

SUMMARY OF THE INVENTION

A diamond surgical blade for clear corneal surgery has distal cutting edges formed by the intersection of a pair of distal anterior bevels with the flat, posterior surface of the blade, with the bevels meeting each other at an angle of about 140° as measured at the posterior surface. Sharpened side edges are formed by a pair of lateral anterior bevels intersecting a pair of lateral posterior bevels. To minimize the tendency of the blade to snag when withdrawn, the blade is rounded at the shoulders at the lateral ends of the distal anterior bevels proximate the side edges.

An elevated shoulder is formed on the anterior surface intermediate the distal and proximal ends of the blade, preferably at a distance of about 1.75 mm from the distal end of the blade and extending to a distance of about 0.1 mm above the distal portion of the anterior surface. When the blade is inserted into the cornea to a distance of about 1.75 mm, the shoulder comes into contact with the corneal tissue and directs the blade in a dimple down motion prior to piercing Descemet's membrane. This allows the surgeon to make the incision using a linear or straight-in motion without changing the angle of the blade to dimple down. The shape of the blade produces a cut or tunnel having a larger surface area than that made by more pointed prior art blades and the sharpened edges resist the tendency to change the shape of the incision as the blade is withdrawn. Rounded blade shoulders formed at the lateral ends of the distal cutting edges tend to prevent the blade from tearing the edges of the incision when withdrawn.

While the following describes a preferred embodiment or embodiments of the present invention, it is to be understood that such descriptions are made by way of example only and are not intended to limit the scope of the present invention. It is expected that alterations and further modifications, as well as other and further applications of the principles of the present. invention will occur to others skilled in the art to which the invention relates and, while differing from the foregoing, remain within the spirit and scope of the invention as herein described and claimed.

BRIEF DESCRIPTION OF THE DRAWINGS

These and further aspects of the present invention will become more apparent upon consideration of the following drawings, in which like numerals indicate like parts, and in which.

DETAILED DESCRIPTION OF THE DRAWINGS

Figure 1:
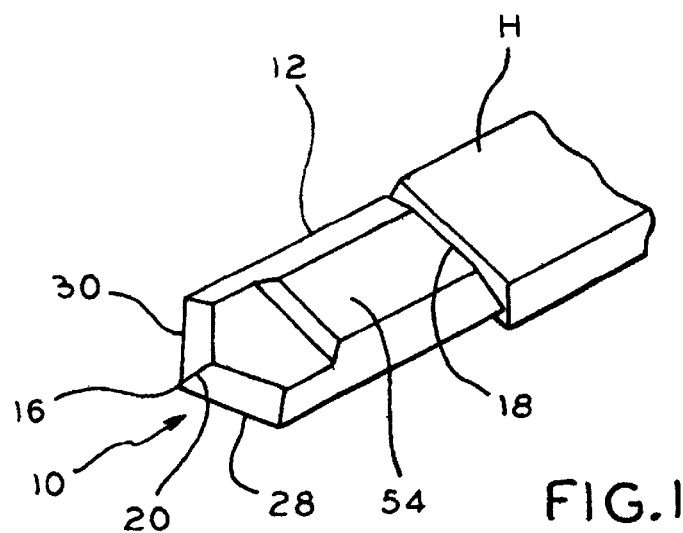
FIG. 1 is a partial perspective view of the surgical blade of the present invention mounted in a blade holder.

Referring now to FIG. 1, the numeral 10 indicates generally a surgical blade embodying the present invention. Blade 10 is particularly adapted for use in ophthalmological surgery and, more particularly, for use in making incisions through the cornea of the eye. While it is possible to manufacture blade 10 from a variety of materials such as, for example, steel, glass, ceramics, precious or semi-precious stones and artificial stones, the blade material preferably comprises diamond and is so illustrated in the accompanying drawings.

Figure 4:
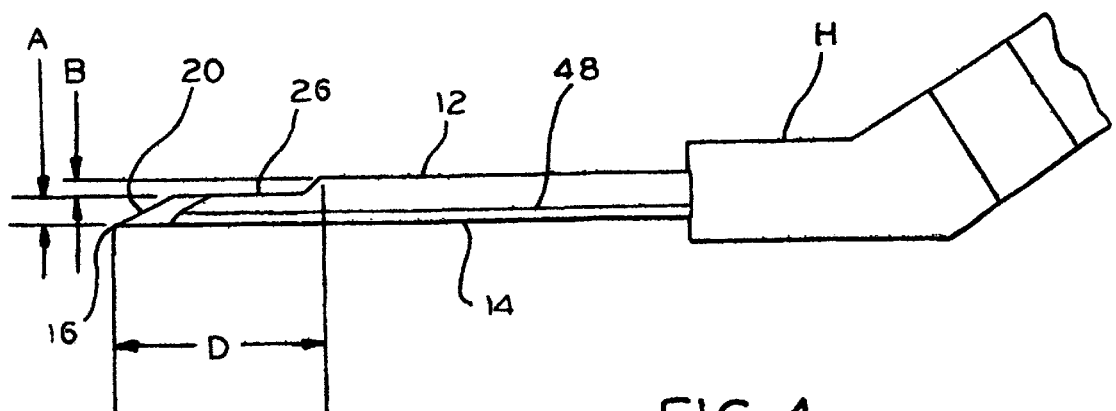
FIG. 4 is a lateral view of the blade of FIG. 1.

As seen in FIGS. 1 and 4, blade 10 has a stepped anterior surface 12 and a flat posterior surface 14. Blade 10 is also configured with a distal piercing end or point 16 and a proximal or handle end 18. As shown in FIGS. 1–4, proximal end 18 is secured to handle H, it being understood that handle H may be in the form of a number of known blade holders presently in use in connection with ophthalmological surgery. While the blade is can be made in varying in sizes and configurations, in the embodiment herein shown blade 10 is approximately 2.5 mm in width and extends a distance of 4.5 mm from the distal end 16 to proximal end 18 at the point where proximal end 18 is secured to holder H.

Figure 2:
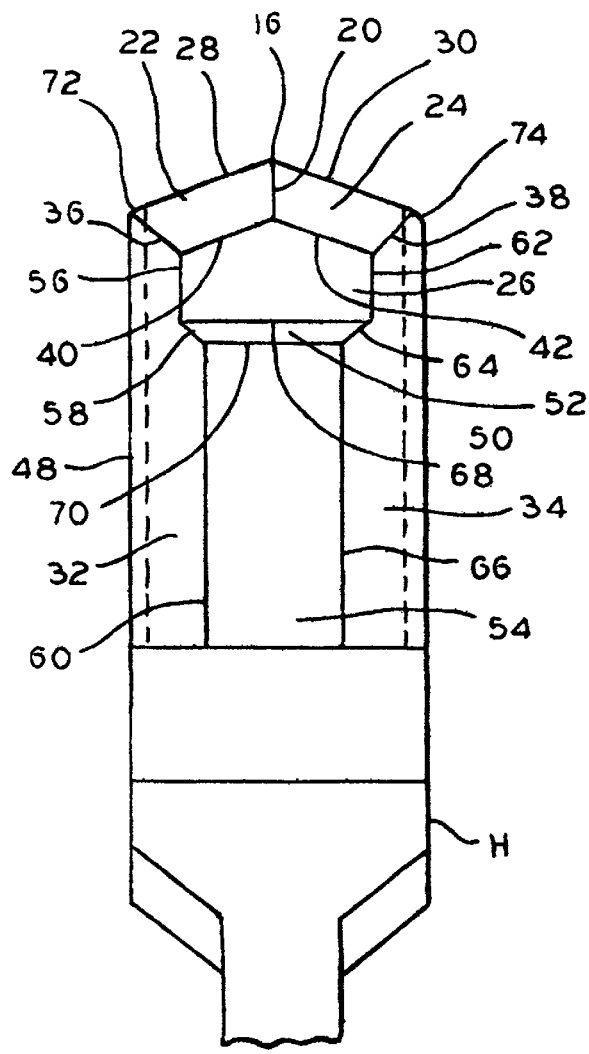
FIG. 2 is a top plan view of the blade of FIG. 1.

In FIG. 2, blade 10 is shown having a first bevel 22 and a second bevel 24 extending from an anterior facet 26 to posterior surface 14. As seen in FIG. 4, anterior facet 26 is parallel to posterior surface 14. The intersection of first bevel 22 and posterior surface 14 forms a first cutting edge 28, while the intersection of second bevel 24 and posterior surface 14 forms a second cutting edge 30. The intersection of bevels 22 and 24 also form distal end or point 16 and a distal ridge 20. In the embodiment herein shown, bevels 22 and 24 are angled such that cutting edges 28 and 30 meet at an angle of approximately 140°. As also seen in FIG. 2, first bevel 22 and second bevel 24 intersect with anterior facet 26 to form, respectively, a first facet edge 40 and a second facet edge 42.

As seen in FIG. 2, blade 10 has a third bevel 32 and a fourth bevel 34 extending longitudinally along blade 10, with third bevel 32 intersecting with first bevel 22 at a shoulder 36 while fourth bevel 34 intersects with second bevel 24 at a shoulder 38.

Figure 3:
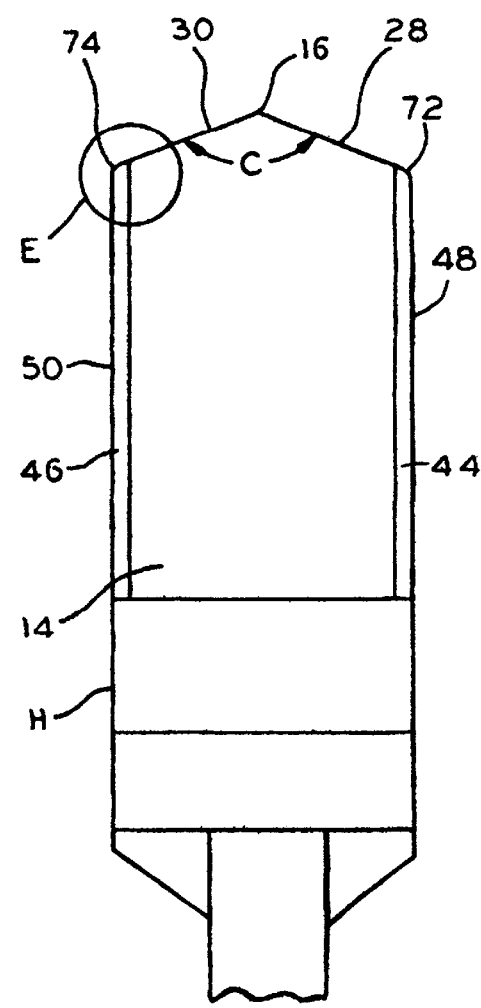
FIG. 3 is a bottom plan view of the blade of FIG. 1.

Referring now to FIG. 3, a fifth bevel 44 is formed on posterior surface 14 as is a sixth bevel 46, with bevels 44 and 46 extending longitudinally along blade 10. The intersection of fifth bevel 44 with third bevel 32 forms third cutting edge 48 while the intersection of sixth bevel 46 with fourth bevel 34 forms fourth cutting edge 50. As seen in FIG. 4, it is a characteristic of the present invention that cutting edges 28 and 30 are coplanar with posterior surface 14 while cutting edges 48 and 50 are in a plane parallel to and slightly above posterior surface 14.

In FIGS. 1 and 2, a transverse bevel 52 is shown extending between anterior facet 26 and an upper shoulder 54. Anterior facet 26 intersects with third bevel 32 to form a first upper edge 56 and with fourth bevel 34 to form fourth upper edge 62. Transverse bevel 52 intersects third bevel 32 to form second upper edge 58 and fourth bevel 34 to form fifth upper edge 64. Shoulder 54 intersects third bevel 32 to form third upper edge 60 and intersects fourth bevel 34 to form sixth upper edge 66. In addition, a lower transverse line 68 is formed to mark the intersection of anterior facet 26 and transverse bevel 52, while the intersection of transverse bevel 52 and upper shoulder 54 forms an upper transverse edge 70.

Figure 6:
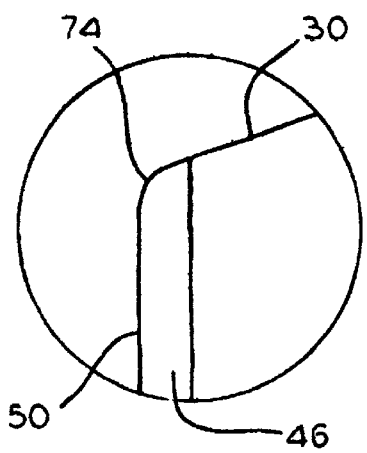
FIG. 6 is an enlarged view of detail E shown in FIG. 3.

In FIGS. 2 and 3 it can be seen that cutting edge 28 is shaped to form a curved or rounded corner 72 where edge 28 meets posterior bevel 44. In like fashion, Detail E of FIG. 3 as seen in FIG. 6 shows edge 30 to have a rounded corner 74 where edge 30 meets posterior bevel 46.

In a preferred embodiment of blade 10, the distance A as shown in FIG. 4 is 0.2 mm while the distance B as shown in FIG. 4 is 0.1 mm. Cutting edges 28 and 30 meet at an angle of approximately 140° when measured at posterior surface 14 as shown at C in FIG. 3. As seen in FIG. 4, distance D extending from distal end 16 to upper transverse edge 70 is preferably 1.75 mm.

Viewing FIGS. 2, 3 and 4 also demonstrates that anterior bevels 32 and 34 are much wider than are posterior bevels 44 and 46 in the preferred embodiment shown, thus positioning lateral cutting edges 48 and 50 closer to posterior surface 14 than to anterior surface 12.

Figure 7:
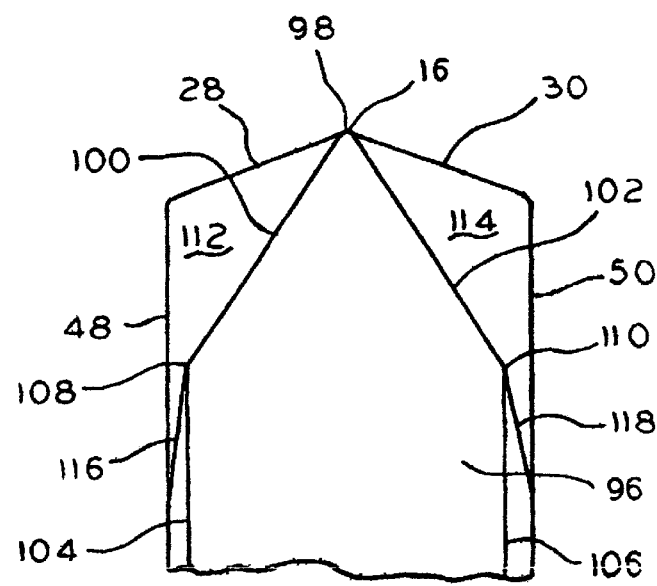
FIG. 7 is a plan view comparison of the surface area of the blade of FIG. 1 and other clear corneal blade configurations.

FIG. 7 is a comparison of the profile of blade 10 with the profiles of the blades shown in Van Heugten, et al., illustrating the relatively larger surface area of blade 10.

Blade 96 corresponds generally to the profile of the blade shown in FIG. 7 of Van Heugten, et al., having a point 98 (coinciding with point 16 of blade 10), a pair of diverging anterior cutting edges 100, 102, a pair of lateral cutting edges 104, 106, with cutting edges 100 and 104 meeting at shoulder 108 and cutting edges 102, 106 meeting at a shoulder 110. The areas 112, 114 of blade 10 demonstrate the increased surface area of blade 10 as compared to blade 96.

A second blade configuration is shown in FIG. 7 of Van Heugten, et al., having a pair of lateral cutting edges 116, 118 diverging from, respectively, shoulders 108, 110. Even with the diverging lateral edges, FIG. 7 clearly illustrates that blade 10 presents a greater surface area than either of the two blade configurations discussed.

Van Heugten, et al. has been selected as representative of similar surgical blades characterized by anterior cutting edges meeting at acute angles and diverging distally. See, for example, FIG. 2 of Van Heugten, et al., illustrating another prior art blade. The comparison of blade profiles is made without considering the other characteristics of the compared blades, such as the presence and sizes of bevels, shoulders and the like.

Use of the present invention may now be described with particular reference to FIG. 5 in which a lateral view of an eye 76 is shown with a cornea 78, a lens 80, an anterior chamber 82 and an iris 84. Principal components of the cornea are the anterior epithelium 86, Bowman's membrane 88 and Descemet's membrane 90. In performing a clear corneal transplant, a lens 80, which may be damaged or diseased, must be removed and a new, artificial lens inserted in its place. To do so, an incision is formed laterally through cornea 78, lens 80 is broken into fragments or emulsified, and the fragments are aspirated through the incision. Thereafter, an artificial lens is inserted through the incision by folding the lens in half and holding the lens in a forceps. After the forceps have been inserted into the incision, the lens is allowed to unfold and is positioned properly within anterior chamber 82.

Critical to the success of such an operation is the making of a self-sealing incision to prevent leakage or loss of fluid from anterior chamber 82. It has been found that the creation of a stepped incision will cause the incision to close upon itself when the operation is complete and will form a watertight seal without requiring the use of sutures. This greatly shortens the healing process as well as the time during which the operation takes place.

Figure 5:
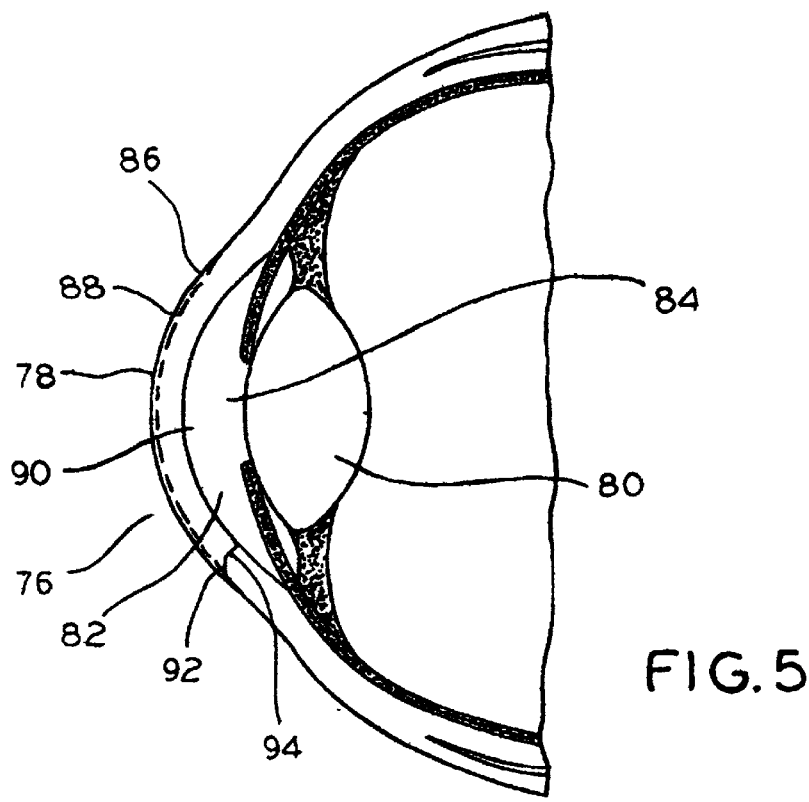
FIG. 5 is a partial lateral sectional view of the human eye.

As seen in FIG. 5, the incision is typically made laterally and, in prior art procedures, a pointed diamond blade is inserted laterally to form the first incision part, or inner corneal valve 92. At some point prior to the cutting of Descemet's membrane 90, the blade would then be angled or "dimpled" down to cut through the remaining corneal tissue along entry 94 and to align the blade 10 at right angles to Descemet's membrane 90 to enter anterior chamber 82. Typically, the thickness of the cornea is about 2.0 mm. Selection of distance D to be 1.75 mm is intended to allow blade 10 to be inserted into the cornea 78 and to have the corneal tissue contact transverse bevel 52 and, thereafter, upper shoulder 54 to create an inner corneal valve 92 of about 1.75 mm in length prior to piercing Descemet's membrane 90. Contact of tissue with upper shoulder 54 forces blade 10 downward to automatically dimple down prior to distal end 16 contacting Descemet's membrane 90. Because of the geometry of blade 10, the dimpling down effect is obtained without requiring the surgeon to change hand positions or estimate the proper angle required to make a perpendicular entry. In addition, the surgeon is not required to gauge or estimate how far blade 10 has been inserted into cornea 78 before the dimpling down must occur.

After blade 10 has been inserted to completely cut through cornea 78, it is then withdrawn and the remaining surgical procedures may be performed to remove and replace lens 80. Rounded shoulders 72, 74 allow blade 10 to be withdrawn without snagging cornea 78 to tear inner corneal valve 92 or entry 94.

As can be seen in the prior art references discussed above, a typical diamond blade used for this type of surgery (such as that shown in Van Heugten et al.) is sharply pointed, that is, the angle between the distal cutting edges is an acute angle and the cutting edges thereafter diverge, eventually reaching the width of cut desired. Thus, the cut is being progressively enlarged as the blade pierces the cornea. When the blade is first inserted, there is a minimum amount of surface area available to support the tissues during the cutting process: it is only as the divergent part of the blade enters the incision, more surface area is made available to support the tissue and guide the blade during the cut. In addition, when a pointed prior art blade pierces into anterior chamber 82, the incision will not extend the fullest width of the blade unless the blade is inserted to bring its widest part into anterior chamber 82.

The present invention, on the other hand, adopts a broader lead cutting edge by having first and second cutting edges 28 and 30 meet at an angle C of approximately 140°. It is believed that the tearing or distortion at the edges of the incision which are suspected to cause leakage are avoided by the cutting surface presented to cornea 78 which supports the corneal tissue over a much larger surface area throughout the incision process and presents an incision having a relatively larger surface area than that made with prior art blades. As blade 10 pierces through to anterior chamber 82, the cut at Descemet's membrane 90 is as wide as the full width of blade 10.

Providing blade 10 with rounded cutting portions 72 and 74 also assures that as the blade 10 is inserted and then subsequently withdrawn, the cutting edges 28, 30 and 48, 50 will not snag or tear the edges of the incision.

While the foregoing examples are presented as preferred embodiments, it should be readily apparent that blades of differing dimensions and configurations may be supplied in instances where the corneal thickness differs from the norm and where it is necessary or desirable to form a wider or narrower incision.

What is claimed is:

1. A surgical knife blade comprising:

an elongated body having a proximal end, a distal end, opposed anterior and posterior surfaces, and first and second opposed longitudinal sides extending between said proximal end and said distal end;

first and second anterior bevels formed at said distal end;

first and second cutting edges located at said distal end, said first and second cutting edges being formed by the intersection of said first and second anterior bevels with said posterior surface, said intersection of said first and second anterior bevels with said posterior surface positioning said first and second cutting edges to be substantially coplanar with said posterior surface at said distal end; and said first and second cutting edges being disposed at an angle greater than 90° with respect to each other as measured in the plane of said posterior surface.

2. The apparatus as recited in claim 1 wherein said blade further comprises a top shoulder formed on and extending a distance above said anterior surface intermediate said distal and proximal ends.

3. The apparatus as recited in claim 2 wherein said angle is 140°.

4. The apparatus as recited in claim 3 wherein said blade further comprises:

a third bevel formed on said anterior surface along said first longitudinal side;

a fourth bevel formed on said anterior surface along said second longitudinal side;

a fifth bevel formed on said posterior surface along said first longitudinal side; and a sixth bevel of formed on said posterior surface along said second longitudinal side, said third and fifth bevels intersecting to form a first side cutting edge and said fourth and sixth bevels intersecting to form a second side cutting edge.

5. The apparatus as recited in claim 4 wherein said third and fourth bevels are wider than said fifth and sixth bevels thereby positioning said first and second side cutting edges closer to said posterior surface than to said anterior surface.

6. The apparatus as recited in claim 5 wherein said first and second side cutting edges lie in a plane parallel to said anterior and posterior surfaces.

7. The apparatus as recited in claim 2 wherein said first cutting edge has a first rounded corner formed thereon proximate the distal end of said first longitudinal side, and said second cutting edge has a second rounded corner formed thereon proximate the distal end of said second longitudinal side.

8. The apparatus as recited in claim 2 wherein said distance above said anterior surface is 0.1 mm.

9. The apparatus as recited in claim 2 wherein said top shoulder is formed on said anterior surface between 1.0 to 2.0 mm from said distal end.

10. The apparatus as recited in claim 9 wherein said top shoulder is formed on said anterior surface 1.75 mm from said distal end.

11. The apparatus as recited in claim 2 further comprising a handle attached to the proximal end of said blade.

12. The apparatus as recited in claim 2 wherein said blade is fashioned from diamond material.

13. A surgical knife blade comprising:

an elongated body having a proximal end, a distal end, opposed anterior and posterior surfaces, and first and second opposed longitudinal sides extending between said proximal end and said distal end;

first and second anterior bevels formed at said distal end;

first and second cutting edges located at said distal end, said first and second cutting edges being formed by the intersection of said first and second anterior bevels with said posterior surface, said intersection of said first and second anterior bevels with said posterior surface positioning said first and second cutting edges to be substantially coplanar with said posterior surface at said distal end; and a top shoulder formed on and extending a distance above said anterior surface intermediate said distal and proximal ends.

14. The apparatus as recited in claim 13 wherein said first and second cutting edges are disposed at an angle greater than 90° with respect to each other as measured in the plane of said posterior surface.

15. The apparatus as recited in claim 14 wherein said angle is 140°.

16. The apparatus as recited in claim 15 wherein said blade further comprises:

a third bevel formed on said anterior surface along said first longitudinal side;

a fourth bevel formed on said anterior surface along said second longitudinal side;

a fifth bevel formed on said posterior surface along said first longitudinal side; and a sixth bevel formed on said posterior surface along said second longitudinal side, said third and fifth bevels intersecting to form a first side cutting edge and said fourth and sixth bevels intersecting to form a second side cutting edge.

17. The apparatus as recited in claim 16 wherein said third and fourth bevels are wider than said fifth and sixth bevels thereby positioning said first and second side cutting edges closer to said posterior surface than to said anterior surface.

18. The apparatus as recited in claim 17 wherein said first and second side cutting edges lie in a plane parallel to said anterior and posterior surfaces.

19. The apparatus as recited in claim 14 wherein said first cutting edge has a first rounded corner formed thereon proximate the distal end of said first longitudinal side, and said second cutting edge has a second rounded corner formed thereon proximate the distal end of said second longitudinal side.

20. The apparatus as recited in claim 13 wherein said distance above said anterior surface is 0.1 mm.

21. The apparatus as recited in claim 13 wherein said top shoulder is formed on said anterior surface between 1.0 to 2.0 mm from said distal end.

22. The apparatus as recited in claim 21 wherein said top shoulder is formed on said anterior surface 1.75 mm from said distal end.

23. The apparatus as recited in claim 14 further comprising a handle attached to the proximal end of said blade.

24. The apparatus as recited in claim 14 wherein said blade is fashioned from diamond material.

* * * * *